US007229789B1

(12) United States Patent
Shepard

(10) Patent No.: US 7,229,789 B1
(45) **Date of Patent: *Jun. 12, 2007**

(54) METHODS AND COMPOSITIONS FOR EXTRACTING PROTEINS FROM CELLS

(75) Inventor: Scot R. Shepard, Clayton, NC (US)

(73) Assignee: N.V. Organon, Oss (NL)

(*) Notice: Subject to any disclaimer, the term of this patent is extended or adjusted under 35 U.S.C. 154(b) by 1641 days.

This patent is subject to a terminal disclaimer.

(21) Appl. No.: 09/766,043

(22) Filed: Jan. 19, 2001

(51) Int. Cl.
*C12N 21/06* (2006.01)
*C12N 1/14* (2006.01)
*C07K 14/00* (2006.01)

(52) U.S. Cl. ............... 435/69.1; 435/255.1; 435/255.5; 435/804; 530/350; 530/412; 530/416; 530/418; 530/422

(58) Field of Classification Search .............. 435/69.1, 435/255.1, 255.5, 804; 530/350, 412, 416, 530/418, 422
See application file for complete search history.

(56) References Cited

U.S. PATENT DOCUMENTS 5,011,915 A 4/1991 Yamazaki
5,407,810 A 4/1995 Builder et al.
6,821,752 B2 * 11/2004 Sheppard .................. 435/69.1

OTHER PUBLICATIONS

Piet, M.P.J. et al: "The use of tri(n-butyl)phosphate detergent mixtures to inactivate hepatitis viruses and human immunodeficiency virus in plasma and plasma's subsequent fractionation" *TRANSFUSION* (1990), 30(7), 591-598.

Horowitz, B. et al: "Inactivation of viruses in labile blood derivatives" *TRANSFUSION* (1985), 25(6), 516-522.

Horowitz, Bernard et al: "Solvent/Detergent-Treated Plasma: A Virus-Inactivated Substitute for Fresh Frozen Plasma" *BLOOD* (1992), 79(3), 826-831.

Helenius, Ari et al: "Solubilization of Membranes by Detergents" *Biochimica et Biophysica Acta*, 415 (1975), 29-79, BBA 85143, The Netherlands.

Potter et al: Production and Purification of the Heavy Chain Fragment C of Botulinum Neurotoxin, Serotype A, Expressed in the Methylotrophic Yeast *Pichia pastoris*; Protein Expression and Purification 19, 393-402 (2000).

Gabay et al: Purification of *Legionella pneumophila* Major Outer Membrane Protein and Demonstration that It Is a Porin; Journal of Bacteriology, Apr. 1985, p. 85-91.

Farrell et al: Effects of Metallothionein on the Observed Copper Distribution in Cell Extracts; Journal of Inorganic Biochemistry, 49, 9-22 (1993).

Leimgruber et al: Development of improved cell lysis, solubilization and imaging approaches for proteomic analyses; Proteomics 2002, 2, 135-144.

Cregg et al: High-Level Expression and Efficient Assembly of Hepatitis B Surface Antigen in the Methylotrophic Yeast, *Pichia pastoris*; Bio/Technology, vol. 5, May 1987.

Potter et al: Production and Purification of the Heavy-Chain Fragment C of Botulinum Neurotoxin, Serotype B, Expressed in the Methylotrophic Yeast *Pichia pastrois*; Protein Expression and Purification 13, 357-365 (1998) Article No. PT980910.

Shepard, Scot R.: Recovery of intracellular recombinant proteins from the yeast *Pichia pastoris* by cell permeabilization; Journal of Biotechnology 99 (2002) 149-160.

* cited by examiner

*Primary Examiner*—Jon Weber
*Assistant Examiner*—Abdel A. Mohamed
(74) *Attorney, Agent, or Firm*—F. Aaron Dubberley

(57) ABSTRACT

A process is disclosed for releasing proteins from cells and/or inactivating viruses. In the process, a host cell containing a protein of interest is contacted with a solution of an effective amount of a detergent.

19 Claims, No Drawings

METHODS AND COMPOSITIONS FOR EXTRACTING PROTEINS FROM CELLS

1. TECHNICAL FIELD OF THE INVENTION

The present invention relates to a process of recovering intracellular proteins and other molecules from a cell.

2. BACKGROUND OF THE INVENTION

It is desirable to lyse cells grown as production hosts containing a protein or other molecule of interest to recover any desired intracellularly produced product. Conventional ways to kill and lyse such cells include the use of heat (U.S. Pat. No. 4,601,986 to Wegner, et al.), osmotic pressure (U.S. Pat. No. 4,299,858 to Aubert, et al), enzymes which break down the cell walls or membranes (U.S. Pat. No. 3,816,260 to Sugiyama, U.S. Pat. No. 3,890,198 to Kobayashi, et al. and U.S. Pat. No. 3,917,510 to Kitamura, et al.) and mechanical disruption of the cell wall by, for example, high pressure homogenization. The disclosures of the above patents are incorporated herein by reference.

Also, detergents have been utilized to lyse the cell wall. For example, yeast protein extraction reagent (Y-PER®), sold by Pierce Chemical Company, contains a detergent to provide a gentle means of cell lysis that is not detrimental to the protein of interest. However, Y-PER® is intended to be used as a laboratory bench reagent, not as a reagent useful for the large scale production of proteins, and is costly. For these reasons, Y-PER® has not gained acceptance as a useful reagent for the large scale production of recombinant protein from host cells.

There is a need in the art for a process that can be used to easily cause the release of proteins from host cells without harming the desired protein and with a minimum of process steps. The method of cell lysis should not directly or indirectly lead to denaturation of the desired product and the method should be consistent with subsequent processing requirements and with large scale production.

3. SUMMARY OF THE INVENTION

The present invention relates to a process of releasing a protein, recombinant or otherwise, from a cell. The process of the present invention involves contacting a host cell containing a protein of interest with a solution comprising one or more detergents. The methods of the invention are particularly suitable to large scale production of recombinant products. The methods of the invention comprise three basic steps: adjustment of bulk solution conditions to achieve a permissive environment, contact of cells with certain charge-modified hydrocarbons, and finally clarification of the extract to produce a fraction suitable for formulation or further processing.

In a particular embodiment, the one or more detergents are amphipathic, charged amines or amine oxides coupled to hydrocarbon chains of varying lengths. In a preferred embodiment, the one or more detergents used are selected from the group consisting of, tributylphosphate, dimethyldecylamine, dimethyltridecylamine, dimethylundecylamine, dimethyldidecylamine, dimethytetradecylamine, dimethylhexadecylamine, dimethyldecylamineoxide, dimethylundecylamineoxide, dimethyldidecylamineoxide, dimethytetradecylamineoxide and dimethyltridecylamineoxide. Preferably, the detergent is not dimethyltridecylamine.

Detergents may be used at concentrations ranging from 0.01% up to their solubility limit. Preferably, the concentration of the detergents ranges from 0.05% to 5%, 0.1% to 2%, or is approximately 0.5% of the total solution. When added to cells suspended in buffer, the detergent is preferably at a higher concentration than the final concentration at which the cells are lysed. Preferably, the detergent is at least at a 2 fold, 5 fold, 10 fold or 100 fold higher concentration In addition to the one or more detergents, in a preferred embodiment, the cells are also contacted with glycerol. Preferably, the glycerol concentration is at least 0.6%, or ranges from 0.6% to 20%, 0.6% to 15%, 0.6% to 12%, 0.6% to 6%, 0.6% to 3%, or 0.6% to 1%.

The pH of the solution can range from pH 2 to pH 12. Preferably, the solution is at a pH ranging from pH 5.0 up to pH 8.0. More preferably, the pH ranges from pH 5.5 to 7.4, from pH 6 to 7.4, from pH 7.0 to 7.4, or is approximately pH 7.3.

The recovery of protein from the cells with the solution of the invention can be carried out at a temperature of from about 2° C. to about 50° C. Preferably, the temperature is from about 2° C. to about 30° C., about 2° C. to about 20° C., about 2° C. to about 10° C., about 3° C. to about 10° C., about 4° C., about 25° C., or at room temperature.

The "host cells" are cells containing a protein of interest. A "protein of interest" is any protein present in a host cell that one desires to release from the host cell and, optionally, subsequently isolate or purify.

Preferably, the protein of interest is a recombinant protein. In a preferred embodiment, the protein of interest has a molecular weight of less than 100 kD. In a further preferred embodiment, the protein of interest has a molecular weight of between 5 and 75 kD, preferably about 50 kD. The host cells may be of any type, preferably mammalian, bacterial, yeast, fungal, plant, avian, or reptilian. Most preferably, the host cells are yeast cells. In a particular embodiment, the yeast cells are of the species *Pichia pastoris*.

In addition to releasing proteins from host cells, the composition of the invention may be used to release other molecules from host cells including nucleic acids, lipids, vitamins, small molecules and other cell, cytosolic, or organelle derived molecules or molecular complexes.

4. DETAILED DESCRIPTION OF THE INVENTION

The present invention relates to a process of releasing a protein, recombinant or otherwise, from a cell. The method of the invention comprises three basic steps: adjustment of bulk solution conditions to achieve a permissive environment, contact of cells with certain charge-modified hydrocarbons, and finally clarification of the extract to produce a fraction suitable for formulation or further processing.

In a particular embodiment, solution conditions are adjusted by 1) sedimentation of the cellular fraction followed by re-suspension, 2) by solution exchange using filtration methods, 3) by direct modification of the existing solution conditions, or 4) by other means of solvent exchange. Cells suspended in an appropriate solution are then contacted with certain amphipathic molecules that cause disruption of the cell membrane thus allowing the cell contents to diffuse through the cell wall and into the extracellular medium. Cellular debris is then separated from the soluble extract by sedimentation, flocculation, filtration, chromatographic, or other separation methods.

In a preferred embodiment, yeast cells, for example *Pichia pastoris*, taken directly from a fermentation process are concentrated and then exchanged from growth medium into a specific buffered solution by tangential flow filtration using microporous membranes. The concentrated and solution adjusted cells are then contacted with dimethylamine and/or dimethylamine oxide compounds with alkyl chains of varying length, depending on cell type and solution conditions. In addition, the solution may contain detergents, such as Triton X-100 or polyols, such as glycerol, that enhance the extraction process. The extract of intracellular molecules is then separated from the remaining insoluble slurry by depth filtration, for example, using diatomaceous earth in a plate and frame filter press.

Solution permissivity is dependent on pH, temperature, ionic strength, time, cell concentration and the addition of certain components that enhance the effectiveness or kinetics of cell disruption or molecular stability. Solution pH can be from pH 3 to 11, more preferably 5 to 8, or approximately 6.5 to 8.0. Temperature can range from about 2° C. to 50° C., or more preferably 2° C. to 30° C. Ionic strength can vary from hypotonic to hypertonic conditions, most preferably 0.001 to 3000 mM sodium chloride, or other salt, depending on the properties of the desired target molecule. In preferred embodiments, the ionic strength is below 350 mM, below 250 mM, below 150 mM, below 100 mM, below 50 mM, and below 10 mM, but not lower than 5 mM, 1 mM, 0.01 mM or 0.001 mM.

The "host cells" are cells containing a protein of interest. A "protein of interest" is any protein present in a host cell that one desires to release from the host cell and, optionally, subsequently isolate or purify. Preferably, the protein of interest is a recombinant protein. When the protein of interest is a recombinant protein, it can be produced by any method known in the art. Typically, a gene that encodes the recombinant protein that is desired is inserted into a recombinant molecule. The polynucleotides constituting the gene may be obtained by standard procedures known in the art, such as from cloned DNA (such as a DNA "library"), chemical synthesis, cDNA cloning, or by the cloning of genomic DNA, or fragment thereof, from a desired cell as described in Sambrook, J., et al., Molecular Cloning: A Laboratory Manual, 2d Edition, Cold Spring Harbor Laboratory Press (1989).

Once the gene encoding the recombinant protein has been isolated, it is inserted into an appropriate cloning vector. A large number of vector-host systems known in the art may be used. Possible vectors include, but are not limited to, plasmids or modified viruses, provided that the vector system is compatible with the host cell used. The vectors that can be used include, for example, an E. coli cloning vector, bacteriophages such as lambda derivatives, plasmids such as pBR322 derivatives or pUC plasmid derivatives. The cloning vector can be introduced into host cells via transformation, transfection, infection, electroporation, etc., so that many copies of the gene sequence are generated.

Transformation of host cells with a cloning vector that incorporates the gene enables the generation of multiple copies of the gene. Therefore, the gene may be obtained in large quantities by growing transformants, isolating the cloning vector from the transformants and, when needed, retrieving the inserted gene from the isolated cloning vector. Once sufficient copies of the gene sequence have been generated, the gene encoding the recombinant protein, or a functionally active fragment or other derivative thereof, can be inserted into an appropriate recombinant molecule. The recombinant molecule is a polynucleotide expression vector that contains the necessary elements for the transcription and translation of the inserted protein-coding sequence of the recombinant protein. Preferably, the expression vector also includes an origin of replication. The necessary transcription and translation signals can also be supplied by the native gene and/or its flanking regions.

Once a recombinant molecule has been prepared, it is inserted into an acceptable host cell which will grow and divide to produce clones. A variety of host cell-vector systems may be utilized to express the recombinant protein. Suitable host cell-vector systems include, for example, bacterial expression systems, mammalian cell systems infected with a virus, such as a vaccinia virus or adenovirus, insect cell systems infected with a virus such as a baculovirus, microorganisms such as yeast containing yeast vectors, and bacteria transformed with bacteriophage DNA, plasmid DNA or cosmid DNA.

Recombinant molecules containing the gene of interest can be identified by PCR amplification of the desired plasmid DNA or specific mRNA, nucleic acid hybridization, presence or absence of marker gene functions and expression of the inserted sequences.

The host cells, such as E. coli cells, transformed with a polynucleotide that encodes a recombinant protein of interest, can be added directly to a reaction vessel. To purify and recover the recombinant protein, the host cells are concentrated to form a concentrated suspension of whole cells. The host cells can be concentrated by any method known in the art. For example, the host cells may be centrifuged. Centrifugation removes water from the host cells and concentrates the cells, forming a cell paste. Centrifugation also separates the host cells from the culture medium. The host cells may be of any type, preferably mammalian, bacterial, yeast, plant, avian, or reptilian. Most preferably, the host cells are yeast cells.

Once a concentrated suspension of cells has been obtained, the cells are contacted with a protein recovery solution. The protein recovery solution comprises one or more detergents. In a particular embodiment, the one or more detergents are amphipathic, charged amines or amine oxides coupled to hydrocarbon chains of varying lengths. In a preferred embodiment, the one or more detergents used are selected from the group consisting of, tributylphosphate, dimethyldecylamine, dimethyltridecylamine, dimethylundecylamine, dimethyldidecylamine, dimethytetradecylamine, dimethylhexadecylamine, dimethyldecylamineoxide, dimethylundecylamineoxide, dimethyldidecylamineoxide, dimethytetradecylamineoxide and dimethyltridecylamineoxide. Preferably, the detergent is not dimethyltridecylamine. Detergents may be used at concentrations ranging from 0.01% up to their solubility limit. Preferably, the concentration of the detergents ranges from 0.05% to 5%, 0.1% to 2%, or is approximately 0.5% or 1% of the total solution. Preferably, the detergents, just prior to their addition to the host cells, are at least 90%, at least 95% or at least 99% pure. In preferred embodiments, the detergents to be added are at least 3 fold, at least 5 fold, at least 10 fold, at least 50 fold, at least 100 fold, at least 200 fold the final concentration of the detergents after addition and dilution in the cell suspension.

In addition to the one or more detergents, in a preferred embodiment, the cells are also contacted with glycerol. Preferably, the glycerol concentration is at least 0.6%, or ranges from 0.6% to 20%, 0.6% to 12%, 0.6% to 6%, 0.6% to 3%, or 0.6% to 1%. Preferably, the glycerol, just prior to addition to the host cells, is at least 90%, at least 95% or at least 99% pure. In preferred embodiments, the glycerol to be added is at least 3 fold, at least 5 fold, at least 10 fold, at least 50 fold, at least 100 fold, at least 166 fold the final concentration of the glycerol after addition and dilution in the cell suspension.

Preferably, the solution is at a pH ranging from pH 5.0 up to pH 8.0. More preferably, the pH ranges from pH 5.5 to 7.4, from pH 6 to 7.4, from pH 7.0 to 7.4, or is approximately pH 7.3.

The recovery of the protein of interest from the cells with the solution of the invention can be carried out at a temperature of from about 2° C. to about 50° C. Preferably, the temperature is from about 2° C. to about 30° C., 2° C. to about 20° C., 2° C. to about 10° C., about 4° C., about 25° C., or at room temperature.

The amount of the detergent solution of the invention used per gram of cells can vary greatly, for example, anywhere from 0.5 mL of detergent solution per gram of cells to 20 mL per gram may be used. Preferably, 2.5–5.0 mL detergent solution per gram of cell paste is used.

The amount of time allowed for lysis of the cells after contacting said cells with the protein recovery solution may be determined by one of skill in the art. For example, cells may be incubated in the presence of the protein recovery solution for 40 minutes up to 72 hours, preferably 90 minutes, 150 minutes, 8 hours or 16–30 hours. Shorter and longer times are also appropriate. In general, the amount of time can be increased when the concentration of detergent is low and decreased when the amount of detergent is high. For example, a protein recovery solution with a 1% detergent concentration is effective after 40 minutes, while a protein recovery solution with a 0.1% detergent concentration should be incubated for 150 minutes or longer. For optimal recovery of protein, the exact amount of time necessary can be determined by a simple time-course experiment at a given concentration of detergent, where concentration of the protein of interest released to the medium is determined over time. After a certain time point, no further increase in released protein will be observed. This time point is the optimal time necessary for lysis of the cells with the chosen concentration of detergent.

After lysis of the cells, the solution can be centrifuged to collect cellular debris in the pellet, leaving the released protein of interest in the supernatant. The supernatant may be processed according to methods known to those of skill in the art to further isolate and purify the protein of interest. The methods utilized to further isolate and/or purify the protein of interest are highly dependent upon the characteristics and properties of the particular protein of interest, and must be determined for each protein.

In a preferred embodiment, the method of the invention is applied to a large scale process of recovering a biomolecule. A large scale process is a process involving large amounts of host cell biomass. In preferred embodiments, the amount of biomass processed in a single batch according to the methods of the invention is from 1 kg to 50,000 kg, 1000 kg to 20,000 kg, 5000 kg to 10,000 kg, or about 40 kg, 100 kg, 1000 kg or 10,000 kg. In another embodiment, the amount of biomass is greater then 1 kg, greater than 40 kg, greater than 100 kg, greater than 1000 kg, greater than 5000 kg, greater than 10,000 kg, or greater than 20,000 kg. The host cells are generally in fermentation broth at the beginning of the process. The host cells are concentrated in the fermentation broth, by, for example, centrifugation or tangential flow filtration, then the fermentation broth exchanged with 60 mM sodium phosphate, 50 mM NaCl, 5 mM EDTA, pH 7.3 (buffer). The exchange can be performed by any means known to one of skill in the art, for example, by tangential flow filtration using 0.45 μm membrane. The concentrated biomass can be maintained at a constant volume while buffer is added to the biomass at a rate equal to the rate at which liquid was removed from the biomass by the filtration process. A buffer exchange of greater than 50%, greater than 60%, greater than 70%, greater than 80%, greater than 90%, 95%, greater than 95% or approximately 100% may be used. Preferably, the exchange is 90% or more. For example, for 7.6 liters of fermentation broth containing approximately 3 kg of cells, approximately 27 L of buffer may be processed as above which results in a buffer exchange of >95%. The concentrated and buffer exchanged biomass is then modified by the addition of detergent and other compounds, for example, glycerol and tetradecyldimethylamine to concentrations of 6.0 and 0.5 final weight percent, respectively. The added compounds may be added separately or mixed and added together. Other concentrations, as recited above, may also be used. The mixture may then be incubated with agitation. This incubation may be for any appropriate time and temperature, for example, for 14.5 h at 19° C. The actual concentrations of detergents, time and temperature for any given extraction may be readily determined by one of skill in the art. After incubation, the soluble fraction of the mixture contains large amounts of protein, nucleic acids, lipids and other molecules previously restricted to the cell membrane and cytoplasm. The mixture may be centrifuged, for example at 4000×g for 30 minutes. The supernatant fraction may then be further processed by, for example, filtration through a 1.2 μm and 0.2 μm filters in series.

The following Examples illustrate the preferred embodiments of the process of the present invention and is not limiting of the specification and claims in any way.

5. EXAMPLES

5.1 Large Scale Release of Recombinant Product

*Pichia pastoris* fermentation broth (12.6 Kg) containing 24.4% biomass by wet weight, having a conductance of 30.2 mS/cm and pH of 4.86, was concentrated to 7.6 L. The concentrated biomass was then exchanged into 60 mM sodium phosphate, 50 mM NaCl, 5 mM EDTA, pH 7.3 (buffer) by tangential flow filtration using 0.45 $m^2$ of 0.45 μm membrane. The concentrated biomass was maintained at 7.6 L while buffer was added to the biomass at a rate equal to the rate at which liquid was removed from the biomass by the filtration process. Approximately 27 L of buffer were processed as above which results in a buffer exchange of >95%. The concentrated and buffer exchanged biomass was then modified by the addition of glycerol and tetradecyldimethylamine, separately, to concentrations of 6.0 and 0.5 final weight percent, respectively. The mixture was then incubated with agitation for 14.5 h at 19° C. At this point the soluble fraction of the mixture contained large amounts of protein, nucleic acids, lipids and other molecules previously restricted to the cell membrane and cytoplasm. The mixture was then centrifuged at 4000×g for 30 minutes. The supernatant fraction was then further processed by filtration through a 1.2 μm and 0.2 μm filters in series. The resulting clarified extract contained approximately 15 g/L of total protein and 0.8 g/L of the specific heterologous protein of interest. The clarified extract also contained significant quantities of ribonucleic acid, deoxyribonucleic acid and cell derived lipids.

5.2 Extraction of Recombinant Product Over Time and at Differing Temperatures

*Pichia pastoris* cells were exchanged into permissive buffer conditions and contacted with 0.5% tetradecyldimethylamine (DMA-C14) and 1% Triton X-100 and 6% glycerol. Samples of the supernatant were taken at various times after incubation at different temperatures, 4° C. and 22° C. The concentration of a specific heterologous (Bot B, or rBoNTB/Hc protein) protein was then determined by an HPLC method specific for that protein. The results are shown in FIGS. 1 (4° C.) and 2 (21° C.). The heterologous is released at higher efficiency over time and at the higher temperature, although at 25 hours, the amount of protein released at the two temperatures were indistinguishable when DMA C14 (tetradecyldimethylamine), triton and glycerol or DMA-C14 and glycerol were used. DMA C14 and Triton and DMA C14 were less effective. Other observations, not represented in FIG. 1 or FIG. 2, show that glycerol, Triton X-100 or buffer alone did not extract protein at a level that was detectable.

5.3 Non-Selective Recovery of Intracellular Biomolecules

*Pichia pastoris* cells were exchanged into permissive buffer conditions and contacted with 0.5% tetradecyldimethylamine (DMA-C14) and 6% glycerol. Samples were taken after incubation and after clarification (low speed centrifugation and 0.2 um filtration). The concentration of RNA, DNA, phospholipids, and total protein were measured using commercially available reagent kits. The concentration of a specific heterologous protein (rBoNTB/Hc) of interest was then determined HPLC. The results are in Table 1.

TABLE 1

| Sample/ assay | RNA (mg/L) | DNA (mg/L) | Phospholipids (mg/L) | Total protein (g/L) | heterologous protein (mg/L) |
|---|---|---|---|---|---|
| extract | 479 | 61 | 1000 | 7.5 | ND |
| clarified extract | <8 ug/mL | 4 | <50 ug/mL | 6.7 | 0.36 |

The data show that RNA, DNA, phospholipids, a specific heterologous protein, and non-specific total protein were extracted from the cells. This shows that the method is non-selective and therefore generally applicable for the recovery in intracellular molecules from microbial cells. The data also show that DNA, RNA, and lipids are easily removed from the soluble protein fraction of the DMA-C14 glycerol extract (compare the extract to the clarified extract). This is in contrast to mechanical cell extraction methods that result in the formation of colloidal suspensions high in nucleic acid and lipid content. Such colloidal materials are not easily separated from the soluble protein fraction and may complicate protein purification methods. Or, on the other hand, severely limit the recovery of DNA, RNA, lipids or similar molecules if those molecules were the molecules of interest. Thus, the gentle, low shear and non-selective feature of the permeabilization method may facilitate the recovery of non-protein intracellular products such as nucleic acids, lipids, and other molecules not readily obtained from mechanical lysates.

Although the invention is described in detail with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

Various publications are cited herein, the disclosures of which are incorporated by reference in their entireties.

What is claimed is:

1. A method of releasing a protein of interest from host cells comprising a. suspending the host cells in a buffer, and b. adding a detergent to the suspended cells wherein the detergent is an amphipathic charged amine or an amphipathic charged amine oxide, and wherein the detergent is in a concentrated form of at least 3 times the desired final concentration of the detergent after dilution in the buffer of step a.

2. A method of releasing a protein of interest from host cells comprising a. suspending the host cells in a buffer, and b. adding a detergent to the suspended cells, wherein the detergent is selected from the group consisting of: tributylphosphate, dimethyldecylamine, dimethyltridecylamine, dimethylundecylamine, dimethyldidecylamine, dimethyltetradecylamine, dimethylhexadecylamine, dimethyldecylamineoxide, dimethylundecylamineoxide, dimethyldidecylamineoxide, dimethyltetradecylamineoxide and dimethyltridecylamineoxide, and wherein the detergent is in a concentrated form of at least 3 times the desired final concentration of the detergent after dilution in the buffer of step a.

3. The method of claim 1, wherein the detergent is not dimethyltridecylamine.

4. The method of claim 3, further comprising the step of adding glycerol to the suspended host cells, and wherein the glycerol is in a concentrated form of at least 3 times the desired final concentration of the glycerol after dilution in the buffer of step 1.

5. The method of claim 4, wherein the detergent comprises a final concentration of between 0.1 to 10 percent.

6. The method of claim 4, wherein the glycerol comprises a final concentration of between 0.6 to 15 percent.

7. The method of claim 5, wherein the glycerol comprises a final concentration of between 0.6 to 6 percent.

8. The method of claim 1, wherein the detergent added is a pure detergent.

9. The method of claim 1, wherein the host cells are at least 1 kg in weight.

10. The method of claim 1, wherein the host cells are *Pichia pastoris* cells.

11. The method of claim 1, wherein the buffer has an ionic strength of less than 350 mM and at least 1 mM.

12. The method of claim 1, further comprising the step of incubating the cell and detergent mixture from 90 minutes to 24 hours.

13. The method of claim 12, wherein the incubation is from 8 hours to 24 hours.

14. The method of claim 1, further comprising the step of incubating the cell and detergent mixture at a temperature of between about 3° C. and about 10° C.

15. The method of claim 2, wherein the detergent is not dimethyltridecylamine.

16. The method of claim 3, further comprising the step of adding glycerol to the suspended host cells, and wherein the glycerol is in a concentrated form of at least 3 times the desired final concentration of the glycerol after dilution in the buffer of step 1.

17. The method of claim 4, wherein the detergent comprises a final concentration of between 0.1 to 10 percent.

18. The method of claim 4, wherein the glycerol comprises a final concentration of between 0.6 to 15 percent.

19. The method of claim 5, wherein the glycerol comprises a final concentration of between 0.6 to 6 percent.

* * * * *